United States Patent [19]

Lazzeri et al.

[11] Patent Number: 5,163,964
[45] Date of Patent: Nov. 17, 1992

[54] ORTHOPAEDIC PROSTHESIS WITH ACCESS IN COLLAR

[75] Inventors: Mark A. Lazzeri; Roy Y. Hori, both of Warsaw, Ind.

[73] Assignee: Zimmer, Inc., Warsaw, Ind.

[21] Appl. No.: 721,730

[22] Filed: Jun. 26, 1991

[51] Int. Cl.⁵ .............................................. A61F 2/32
[52] U.S. Cl. ......................................... 623/23; 606/86
[58] Field of Search ....................... 623/16, 18, 19, 20, 623/22, 23; 606/84, 86, 99

[56] References Cited

U.S. PATENT DOCUMENTS

| | | | |
|---|---|---|---|
| 2,765,787 | 10/1956 | Pellet | 128/92 |
| 3,036,482 | 5/1962 | Kenworthy et al. | 606/84 |
| 3,781,917 | 1/1974 | Mathys | 623/23 |
| 3,814,089 | 6/1974 | Deyerle | 623/23 |
| 3,859,669 | 1/1975 | Shersher | 3/1 |
| 4,399,813 | 8/1983 | Barber | 128/92 EC |
| 4,406,023 | 9/1983 | Harris | 623/18 |
| 4,476,861 | 10/1984 | Dimakos et al. | 128/303 R |
| 4,514,865 | 5/1985 | Harris | 623/18 |
| 4,612,922 | 9/1986 | Barber | 128/92 EB |
| 4,623,353 | 11/1986 | Buechel et al. | 623/23 |
| 4,642,121 | 2/1987 | Keller | 623/18 |
| 4,678,471 | 7/1987 | Noble et al. | 623/23 |
| 4,702,236 | 10/1987 | Tarabichy et al. | 128/92 V |
| 4,770,660 | 9/1988 | Averill | 623/23 |
| 4,846,161 | 7/1989 | Roger | 128/92 V |
| 4,865,609 | 9/1989 | Roche | 623/23 |
| 4,873,969 | 10/1989 | Huebsch | 128/92 R |
| 4,904,262 | 2/1990 | Bensmann | 623/23 |
| 4,919,153 | 4/1990 | Chin | 606/93 |
| 4,986,826 | 1/1991 | Roger | 606/82 |
| 5,019,083 | 5/1991 | Klapper et al. | 606/99 |
| 5,047,034 | 9/1991 | Sohngen | 606/96 |

FOREIGN PATENT DOCUMENTS

0399530A2 11/1989 European Pat. Off. .
0393608A2 10/1990 European Pat. Off. .

OTHER PUBLICATIONS

"The Hall Revision Surgery System"—Amsco/Hall Surgical—Zimmer—Lit. No. 83-011-0000-02-37—1983.
"Hall Stem Extractor System"—Amsco/Hall Surgical—Zimmer—Lit. No. 83-011-5044-0248—1983.
"Cement Removal Utilizing the CEBOTOME Bone Drill in Revision Hip Arthroplasty—Surgical Technique"—Zimmer—Lit. No. 85-057-5052-0963—1981.
Waldemar Link/Bard—Sample Trial Hip for 161013—1981/82.

Primary Examiner—David Isabella
Attorney, Agent, or Firm—Margaret L. Geringer

[57] ABSTRACT

An orthopaedic prosthesis for implanation in a bone, the prosthesis including a collar extending outwardly therefrom. The collar includes an access recess aligned above the bone cement when the stem is implanted with cement in bone, or aligned above the bone/implant interface when the stem is biologically affixed to the bone. The access recess may be a dimple partially extending into the collar or it may be a through hole. The dimple provides a preset drill start for a drill to be aligned therewith for drilling through the collar to form a hole therethrough. In either case, whether starting with a dimple and then forming a hole or starting directly with a through hole, the hole may be progressively enlarged by use of sequentially larger drill sizes. Tools, such as chisels or the like, are inserted through the hole in the collar to break up the bone cement beneath the collar if a cemented stem, or to help break the bond between the stem and the bone if a biologically affixed stem, to help loosen the prosthesis from the bone to facilitate removal of the stem. A method of removing such a prosthesis is also disclosed.

8 Claims, 2 Drawing Sheets

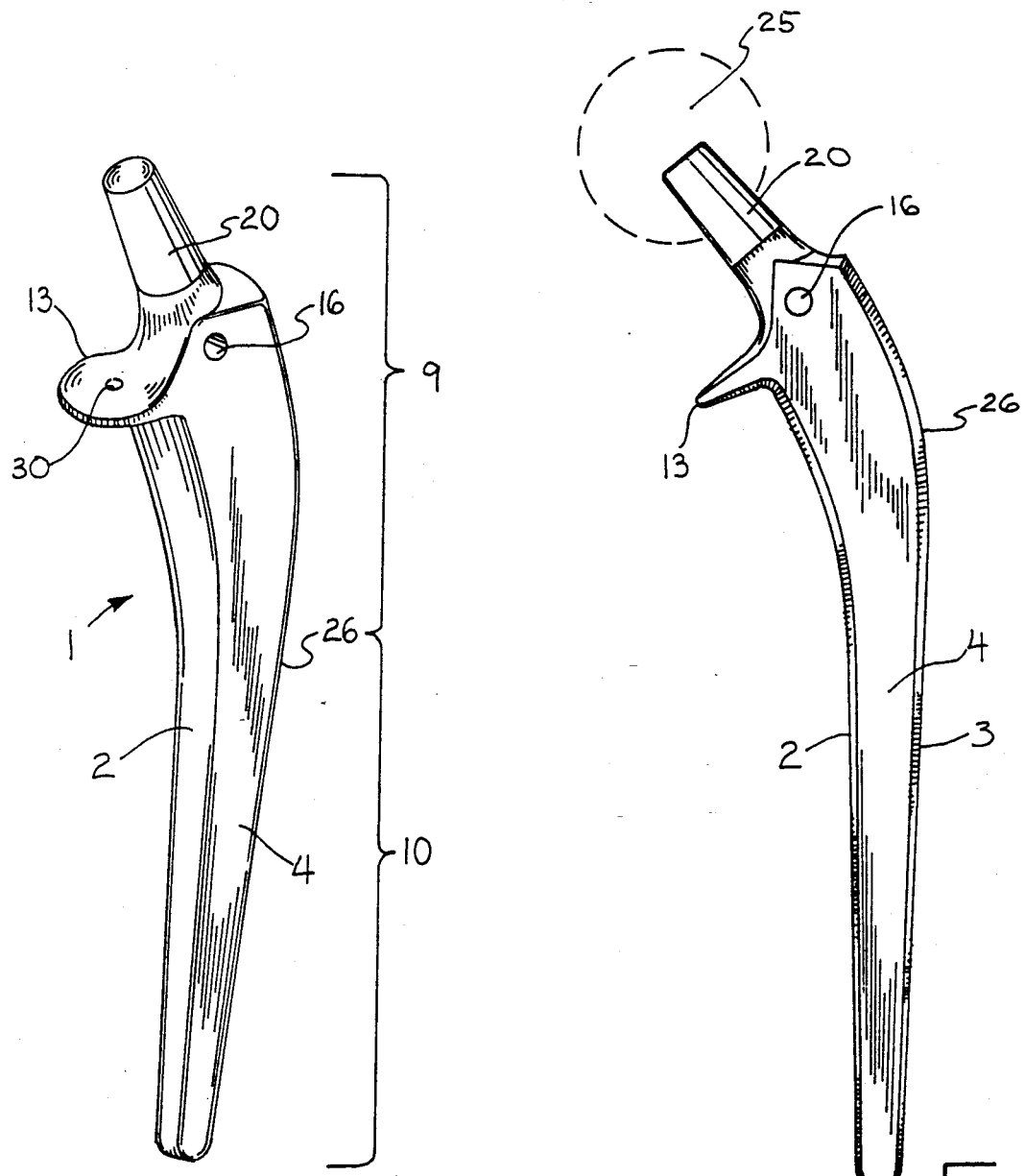
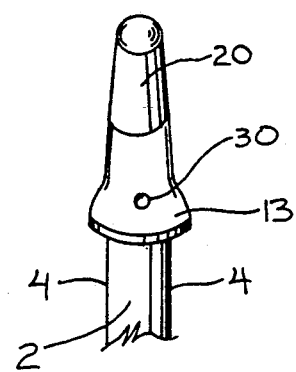
Fig. 1
Fig. 2
Fig. 3

ORTHOPAEDIC PROSTHESIS WITH ACCESS IN COLLAR

BACKGROUND OF THE INVENTION

The present invention relates to an orthopaedic prosthesis, and more particularly to a prosthesis with an access recess in the collar to facilitate loosening and subsequent removal of the stem from the bone.

It is known that orthopaedic prostheses may be secured into a bone with bone cement. There are times when it becomes necessary to remove a cemented prosthesis from the bone, and thus the prosthesis must be loosened from the cement. The cement generally forms a layer having a thickness between the bone and the prosthesis. It is well known in the art of orthopaedics to provide prostheses, such as femoral hip stem components, with collars or without collars. Collars typically extend outwardly from the stem in order to engage with or rest on the bone surrounding the cavity prepared for the stemmed implant. Some stems have no extending collar, while others have a circumferential collar extending from and surrounding all sides of the prosthesis, while others just have a collar extending on one or more selected sides, for example, extending just from the medial side. When it is determined necessary to remove a cemented stem from the bone, various tools, such as chisels or other suitable instruments, can be inserted between the prosthesis and bone into the cement to break up the cement and loosen the prosthesis from the cement. However, when a prosthesis includes an extending collar, it is difficult to break up the cement directly below the collar because it is not readily accessible.

It is also known to secure prosthetic implants without bone cement, such as by a press-fit or by biological ingrowth of bone into textured or porous surfaces or the like. If such prosthesis necessitates removal, the biological ingrowth bond to the implant must be broken to remove the implant. If there is an extending collar over portions of the stem affixed by biological ingrowth, it is difficult to break this bond directly below the collar because this portion is not readily accessible.

One way of dealing with this difficulty is described by U.S. Pat. No. 4,770,660 which provides a removable collar to enable access to the affixed surfaces of the implant beneath the collar. Another option is provided in U.S. Pat. Nos. 4,406,023 and 4,514,865 to Harris which discloses an implant which utilizes an enhanced fixation surface (either for biological fixation in '023 or cemented fixation in '865) only on the surfaces of the implant not directly beneath the extending collar.

Other devices are known for assisting with the removal of prostheses from a bone cavity. U.S. Pat. No. 4,919,153 to Chin discloses a ball clamp 32 connected to a slap hammer 22 for clamping about the head of a femoral component to pull the femoral component from the cement mantle. U.S. Pat. Nos. 4,612,922 and 4,399,813 to Barber disclose an apparatus for drilling into a prosthesis embedded in a bone shaft. The drilling apparatus of Barber has particular application to drilling into the end of a fragment of an elongated prosthesis which remains embedded in bone after fracture of the prosthesis.

Various tools and methods for removing the bone cement itself from the bone cavity are disclosed in the following U.S. Pat. Nos.: 5,019,083; 4,986,826; 4,873,969; 4,846,161; 4,702,236; 4,476,861.

OBJECTS OF THE INVENTION

A principal object of the invention is to provide an orthopaedic prosthesis which includes an access recess in the collar.

A further object of the invention is to provide a method for accessing the bone cement beneath the collar of an implanted cemented prosthesis in order to break up the cement to loosen the prosthesis from the cement.

A still further object of the invention is to provide a method for accessing the biologically affixed area beneath the collar of a biologically affixed prosthesis in order to break this bond with the implant to loosen this implant from the bone.

Another object of the invention is to provide a prosthesis and a method of loosening and removing an affixed prosthesis from a bone cavity by enabling removal instruments to be inserted through an opening in an extending collar of the prosthesis.

SUMMARY OF THE INVENTION

The present invention provides an orthopaedic prosthesis for implantation in a bone, the prosthesis including a collar extending outwardly therefrom. The collar includes an access recess aligned above the bone cement when the stem is implanted with cement in bone, or aligned above the bone/implant interface when the stem is biologically affixed to the bone. The access recess may be a dimple partially extending into the collar or it may be a through hole. The dimple provides a preset drill start for a drill to be aligned therewith for drilling through the collar to form a hole therethrough. In either case, whether starting with a dimple and then forming a hole or starting directly with a through hole, the hole may be progressively enlarged by use of sequentially larger drill sizes. Tools, such as chisels or the like, are inserted through the hole in the collar to break up the bone cement beneath the collar if a cemented stem, or to help break the bond between the stem and the bone if a biologically affixed stem, to help loosen the prosthesis from the bone to facilitate removal of the stem. A method of removing such a prosthesis is also disclosed.

BRIEF DESCRIPTION OF THE DRAWINGS

These features and other objects of the invention, as well as others, will become apparent to those skilled in the art by referring to the accompanying drawings:

FIG. 1 is a perspective view of a hip stem implant according to the present invention;

FIG. 2 is a side elevation view of the hip stem of FIG. 1;

FIG. 3 is a partial front elevational view of the hip stem of FIG. 1;

DETAILED DESCRIPTION OF THE INVENTION

Figure 4:
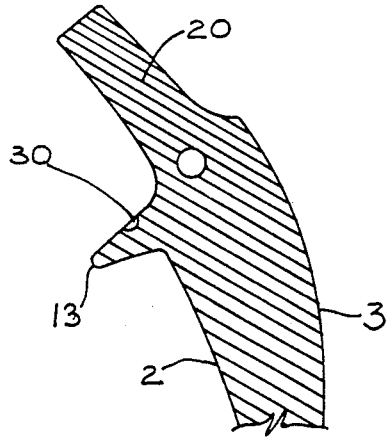
FIG. 4 is a partial side elevational view of the hip stem of FIG. 1 shown in cross-section.

FIGS. 1-8 illustrate a particularly advantageous embodiment of an orthopaedic implant according to the present invention. The invention will be described with reference to a cemented hip prosthesis implant; however, it is understood that the principles of the invention are applicable to any suitable stemmed prosthetic implant having a collar.

The prosthetic hip implant 1 of FIGS. 1-8 includes a stem 26 having a proximal portion 9 and a distal portion 10. The stem 26 includes a pair of approximately opposite side walls 4 separated by a medial side 2 and a lateral side 3. The hip implant 1 includes a collar 13 extending outwardly from the upper end of the medial side 2 just below the transition to the neck 20 of the stem 26. In addition, a through hole 16 may be provided in the uppermost portion of the proximal portion 9 to engage a suitable instrument in order to facilitate stem extraction, as is known in the art.

FIG. 2 illustrates a separate head 25 shown in phantom lines and mounted on the neck 20. It is well known in the art that the head portion 25 may be a separate component from the stem, as shown, or it may be integrally formed with the stem 26.

Figure 5:
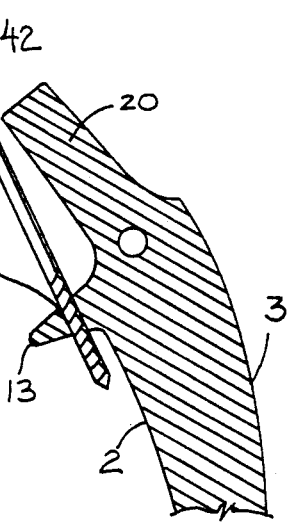
FIG. 5 is a partial side elevational view of the hip stem of FIG. 4 shown in cross-section and illustrating a drill in association therewith.
Figure 6:
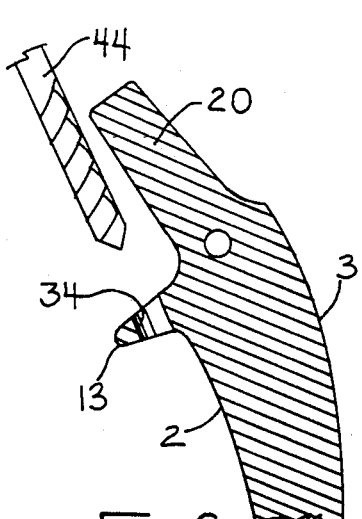
FIG. 6 is a partial side elevational view of the hip stem of FIG. 5 shown in cross-section and illustrating a larger size drill in association therewith.
Figure 7:
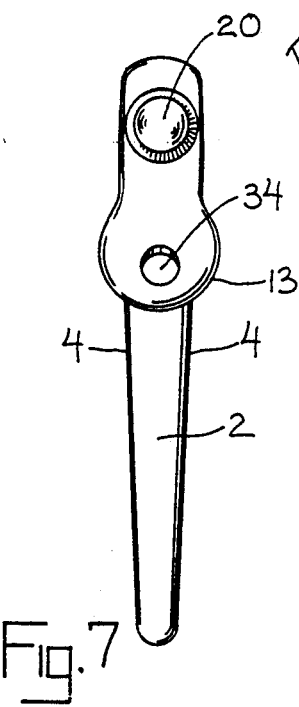
FIG. 7 is a top plan view of the hip stem of FIG. 6 viewed looking down at the top surface of the neck.
Figure 8:
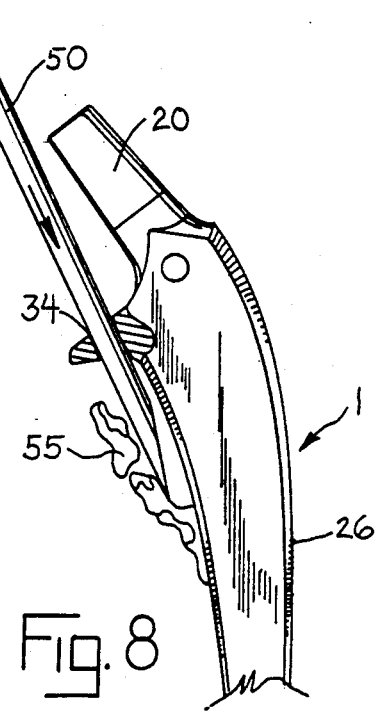
FIG. 8 is a partial side elevational view of the hip stem of FIG. 7 shown in partial cross-section and illustrating a cement breaking tool in association therewith.

The collar 13 of the hip implant 1 includes an access recess which may be in the form of a dimple 30 partially extending into the collar as shown in FIGS. 1-4 or it may be a through hole 32 as shown in FIG. 5. The dimple 30 provides a preset drill start for a first drill 42 to be aligned with the dimple for drilling through the collar 13 to form a hole 32 therethrough. Alternatively, the access recess may be a preformed hole 32 therethrough. In either case, whether starting with a dimple 30 and then drilling or forming the hole 32 from the dimple or whether starting directly with the through hole 32 already formed in the collar 13, the hole may be progressively enlarged by use of one or more sequentially larger drills 44 to form a larger hole 34.

Then tools such as a chisel 50 may be inserted through the hole 34 or 32 in the collar to break up the bone cement 55 beneath the collar 13 to help loosen the hip implant 1 from the cement 55 to facilitate removal of the cemented stem. The chisel 50 may have a sharp tip to assist with breaking up the cement. Once the hip implant 1 is loose enough from the cement 55, the hip implant 1 may be removed from the bone cavity by any suitable means. For example, an elongated rod (not shown) may be inserted through the hole 16 in stem 26 and upward force applied to remove the stem 26 from the bone cavity. It is understood that in the case of an implant that is biologically affixed rather than cemented, the tools may be inserted through the hole 34 or 32 in the collar to break the interface or bond between the bone and the stem.

Although only one access recess is shown, it is understood that a plurality of access recesses could be provided if desired. This would be particularly advantageous if the collar 13 extended outwardly from the stem 26 on more than one side of the stem.

The method of removing the cemented prosthesis or cemented hip implant 1 will be described with reference to the access recess being a dimple 30 extending partially through the collar 13 from the top side. A first drill 42 is aligned with the preset drill start or dimple 30. The dimple 30 is positioned so that it is aligned above the cement in the bone. The drill 42 is then drilled through the collar 13, so that it penetrates the underside of the collar 13 forming a through hole 32 to provide access via hole 32 to the cement 55. Alternatively, the hip implant 1 may be initially manufactured with the access recess being a through hole 32 rather than dimple 30. In either case, a second drill 44 having a larger diameter than the first drill 42 is aligned with hole 32. The drill 44 is then drilled through the collar 13 to provide a larger hole 34. This may be done with further subsequently larger diameter drills as required to remove more material from the collar 13. A tool such as a chisel 50 may be inserted through hole 34 or 32 to break up the bone cement 55 beneath the collar 13. The cement 55 may also be penetrated by and broken up by the drills 42 or 44 as they drill through the collar 13.

The prosthesis of the present invention may be manufactured from any suitable biologically acceptable material. Such materials include, but are not limited to, a cobalt-chromium alloy or a titanium alloy or any other medical grade materials suitable for prostheses. The implant may be formed by forging or casting or any other appropriate manufacturing processes.

The width of the dimple 30 may be about 2 to 3 mm with a depth into the collar 13 of about 1 to 2 mm. The collar 13 shown in FIG. 4 may be as thick as 5 to 6 mm at its thickest portion. The first drill 42 (and thus hole 32) may be about 2 to 3 mm corresponding to the width of the dimple 30. The second drill 44 may be about 1 to 2 mm greater than the first drill 42. If more than two incremental drill sizes are used to enlarge the cement access recess, they may suitably increase in size by about 1 to 2 mm increments. Drilling may preferably be done by progressive steps rather than drilling the final size at once to minimize heat build up. The final hole width may be up to 6 to 8 mm in diameter, as desired. The collar 13 may be 15 to 20 mm across in width and length. However, it is noted that these dimensions are not intended to be limiting features, as any suitable dimensioning may be provided. Also, the size and shape of the prosthesis itself may also utilize any suitable features and dimensioning as desired.

The access recess feature on the collar of a stemmed prosthesis facilitates prosthesis removal by allowing access to the area underneath the extending collar, so that the bond interface between the implant and bone (whether a cement interface or a biological fixation interface) can be broken up by the drills or other tools to dislodge the stem from the bone when removal of a prosthesis with a collar extending on one or more sides is determined to be necessary. The access recess may be either a preformed hole in the collar or a preset dimple to locate a drill for drilling a hole through the collar. The access recess is substantially aligned above the bone/implant interface and oriented from the top side of the collar downward toward this interface. The hole may be enlarged as needed with larger drill sizes. The hole in the collar then provides access for tools to reach this interface underneath the collar to assist in breaking up this interface to help loosen the prosthesis from the bone, so that the prosthesis may be extracted from the bone cavity. It is noted that if the tool, such as 50, is smaller in diameter than the final hole diameter, the tool can be angled about to reach a greater area below the collar.

While this invention has been described and exemplified in terms of a particularly advantageous embodiment, those skilled in the art can appreciate that modifications can be made without departing from the spirit and scope of the invention.

We claim:

1. A method of removing an orthopaedic prosthesis from a bone wherein the prosthesis is affixed to the bone by a bond interface therebetween and wherein the prosthesis includes an elongated stem and a collar extending outwardly from an upper end of the stem, the collar including an access recess therein positioned on the collar so that the access recess is substantially aligned above the bond interface in the bone, the method comprising the following steps:
   a) aligning a first drill with the access recess; and
   b) drilling through the access recess with said first drill through the collar to access the bond interface.

2. The method of claim 1 further comprising:
   a) aligning a second drill having a larger diameter than the first drill with the access recess; and
   b) drilling through the access recess with said second drill to enlarge the access recess.

3. The method of claim 1 further comprising the step of inserting a tool through the access recess to break up the bond interface beneath the collar.

4. The method of claim 2 further comprising the step of inserting a tool through the access recess to break up the bond interface beneath the collar.

5. A method of removing an orthopaedic prosthesis from a bone wherein the prosthesis is affixed to the bone by a bond interface therebetween, and wherein the prosthesis includes an elongated stem and a collar extending outwardly from an upper end of the stem, the collar including an access recess therein positioned on the collar so that the access recess is substantially aligned above the bond interface in the bone, the method comprising the following steps:
   a) aligning a first drill with the access recess; and
   b) drilling through the access recess with said first drill to remove material from the collar to form a hole through the collar to access the bond interface.

6. The method of claim 5 further comprising:
   a) aligning a second drill having a larger diameter than the first drill with the hole; and
   b) drilling through the hole with said second drill to remove additional material from the collar to enlarge the hole.

7. The method of claim 6 further comprising the step of inserting a tool through the hole to break up the bond interface beneath the collar.

8. A method of removing a cemented orthopaedic prosthesis from a bone wherein the prosthesis includes an elongated stem embedded in bone cement and a collar extending outwardly from an upper end of the stem, the collar including a cement access recess therein positioned on the collar so that the cement access recess is aligned above the cement in the bone, the method comprising the following steps:
   a) aligning a first drill with the cement access recess; and
   b) drilling through the cement access recess with said first drill through the collar to access the bone cement.

* * * * *